United States Patent
Zhou et al.

(10) Patent No.: US 8,586,913 B2
(45) Date of Patent: Nov. 19, 2013

(54) FLUIDIC DENSITY MEASUREMENTS BASED ON BETA PARTICLES DETECTION

(75) Inventors: Zilu Zhou, Needham, MA (US); Christopher Harrison, Auburndale, MA (US); Bradley A. Roscoe, Ridgefield, CT (US); Chloe Coleou, Neuilly-Plaisance (FR); Douglas W. Grant, Cedar Creek, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 22 days.

(21) Appl. No.: 12/987,586

(22) Filed: Jan. 10, 2011

(65) Prior Publication Data

US 2012/0175510 A1   Jul. 12, 2012

(51) Int. Cl.
*G01N 23/12* (2006.01)
(52) U.S. Cl.
USPC .......................................... 250/255; 250/253
(58) Field of Classification Search
USPC ........................................................ 250/308
See application file for complete search history.

(56) References Cited

U.S. PATENT DOCUMENTS

| | | | |
|---|---|---|---|
| 2,899,555 A * | 8/1959 | Fries | 250/383 |
| 3,621,257 A * | 11/1971 | Johnston et al. | 250/370.01 |
| 4,682,034 A | 7/1987 | Saint et al. | |
| 4,835,390 A | 5/1989 | Blatchley et al. | |
| 4,924,099 A | 5/1990 | Lim et al. | |
| 5,099,504 A | 3/1992 | Pettit | |
| 5,566,686 A * | 10/1996 | Grossbach et al. | 131/84.4 |
| 5,568,818 A * | 10/1996 | Neri et al. | 131/84.4 |
| 5,591,644 A | 1/1997 | Karmen | |
| 5,854,684 A | 12/1998 | Stabile et al. | |
| 5,872,623 A | 2/1999 | Stabile et al. | |
| 6,214,191 B1 | 4/2001 | Wiktorowicz et al. | |
| 6,379,929 B1 | 4/2002 | Burns et al. | |
| 6,639,210 B2 * | 10/2003 | Odom et al. | 250/269.6 |
| 6,640,625 B1 * | 11/2003 | Goodwin | 73/152.05 |
| 7,075,062 B2 * | 7/2006 | Chen et al. | 250/269.1 |

(Continued)

FOREIGN PATENT DOCUMENTS

| | | |
|---|---|---|
| JP | 1987239047 A | 10/1987 |
| WO | 2004095061 A2 | 11/2004 |

OTHER PUBLICATIONS

International Search Report and Written Opinion of PCT Application No. PCT/US2012/020615 dated Aug. 27, 2012: pp. 1-14.

(Continued)

*Primary Examiner* — Marcus Taningco
(74) *Attorney, Agent, or Firm* — Jakub Michna; Rachel E. Greene; Bridget Laffey

(57) ABSTRACT

Devices, methods, and related systems are described for measuring a property of a fluid, including density, in a subterranean environment. A device includes a pressure housing having one or more windows formed in the pressure housing and a flow device arranged in the pressure housing for the fluid to flow through the flow device. Further, a radiation source is mounted within the pressure housing approximate a first source window configured to generate particles into the fluid. The device includes a detector supported by the pressure housing and positioned approximate a first detector window of the one or more windows. The first detector window is located between the detector and the flow device. The detector can be a solid state beta particle detector with a wide band gap, such as the diamond detector, and the radiation source can be a beta particle source, such as a strontium 90 source.

43 Claims, 9 Drawing Sheets

(56) References Cited

U.S. PATENT DOCUMENTS

| | | |
|---|---|---|
| 7,279,678 B2 | 10/2007 | Andrews et al. |
| 7,316,899 B2 | 1/2008 | McDevitt et al. |
| 7,387,159 B2 | 6/2008 | Fitzgerald |
| 7,461,547 B2 * | 12/2008 | Terabayashi et al. ...... 73/152.55 |
| 7,576,856 B2 * | 8/2009 | DiFoggio ...................... 356/328 |
| 7,686,499 B2 | 3/2010 | Dykstra et al. |
| 7,800,070 B2 | 9/2010 | Weinberg et al. |
| 8,146,655 B2 * | 4/2012 | Indo et al. ................ 166/250.01 |
| 2004/0258615 A1 | 12/2004 | Buchanan et al. |
| 2004/0262158 A1 | 12/2004 | Alvord et al. |
| 2005/0136548 A1 | 6/2005 | McDevitt et al. |
| 2008/0041593 A1 * | 2/2008 | Brown et al. ................. 166/302 |
| 2008/0149819 A1 | 6/2008 | Zhdaneev |
| 2009/0057545 A1 | 3/2009 | Saenger et al. |
| 2009/0321072 A1 * | 12/2009 | Kanayama et al. ...... 166/250.01 |
| 2009/0321622 A1 * | 12/2009 | Stoller ....................... 250/269.3 |
| 2010/0025574 A1 | 2/2010 | Georgi et al. |
| 2010/0268469 A1 | 10/2010 | Harrison et al. |
| 2010/0282959 A1 * | 11/2010 | Dong et al. ................. 250/269.1 |
| 2011/0284731 A1 | 11/2011 | Roscoe et al. |

OTHER PUBLICATIONS

Berger et al., "Stopping-Power and Range Tables for Electrons, Protons, and Helium Ions," NIST Physical Measurement Laboratory, Oct. 2009: pp. 1-12, <http://www.nist.gov/pml/data/star/index.cfm>.

McCain, Jr., "Chapter 1: Components of Naturally Occurring Petroleum Fluids," The Properties of Petroleum Fluids, Second Edition, PenWell Publishing Company: Oklahoma, 1990: pp. 1-45.

Mullins et al., "Compartment Identification by Downhole Fluid Analysis," Petrophysics, Aug. 2005, vol. 46(4): pp. 302-312.

Knoll, "Chapter 2: Radiation Interactions," Radiation Detection and Measurement, Third Edition, John Wiley & Sons, Inc.: New Jersey, 2000: pp. 29-64.

* cited by examiner

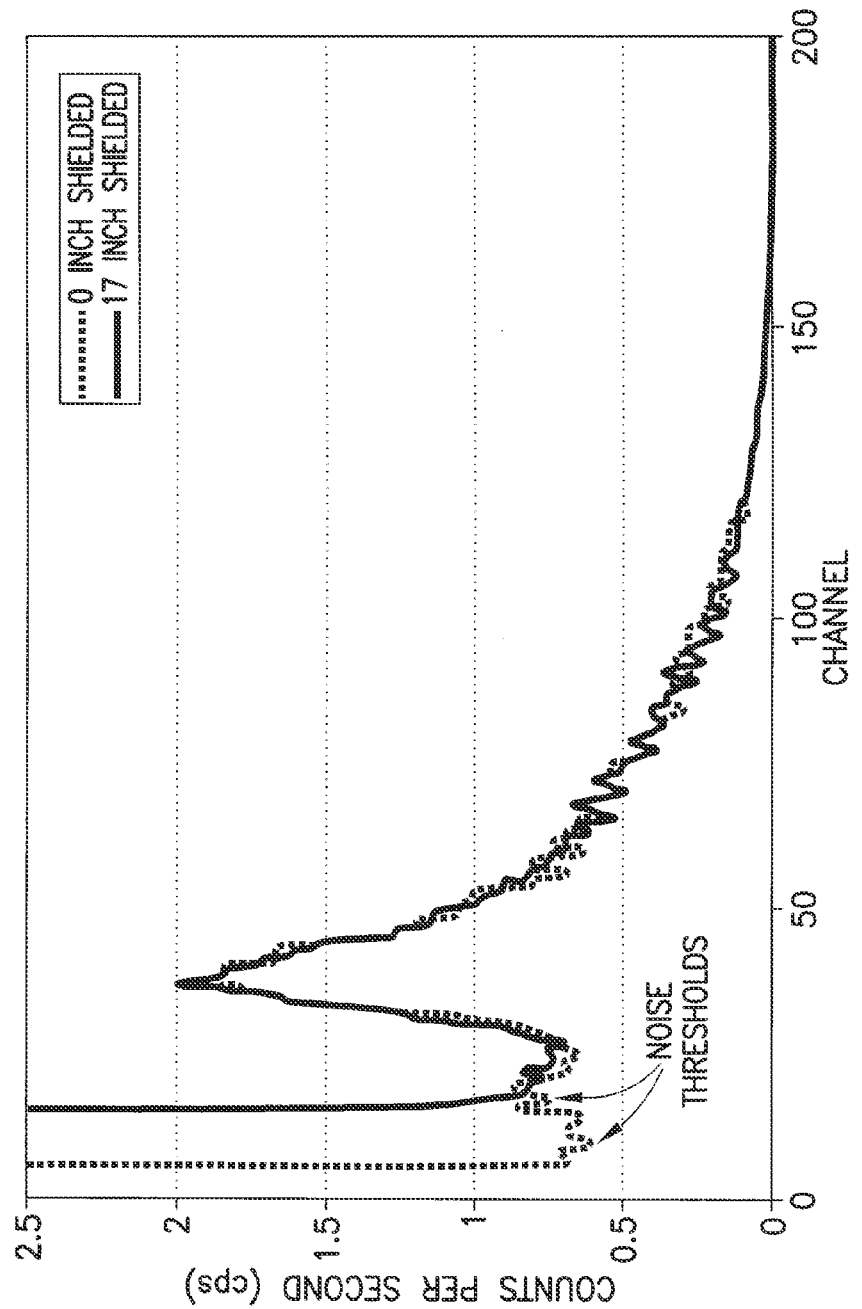

FLUIDIC DENSITY MEASUREMENTS BASED ON BETA PARTICLES DETECTION

BACKGROUND

1. Field

This patent relates generally to devices and methods for measuring fluid properties for oilfield and other industrial applications. In particular, the patent relates to measuring one or more fluid properties such as density.

2. Background

The ability to measure fluid density and other fluid properties downhole is paramount to petroleum exploration as it enables one to differentiate between oil, gas, and water. W. D. McCain, Jr., *The Properties of Petroleum Fluids*, $2^{nd}$ ed. (1990). The relative amounts of oil and gas produced have a direct impact on reservoir development cost. Furthermore, it allows one to locate the oil-water contact line and hence the thickness of the pay zone of a formation. This ability hinges upon the availability of an accurate and robust sensor that works reliably in the harsh environment found in an oil well. Oilfield pressures downhole may be as high as 25,000 psi with temperatures up to 175° C. or higher. There are wells with even more extreme conditions, especially offshore. A further challenge in downhole fluid analysis is that acquiring large quantities of representative downhole fluids is difficult due to ever-present contamination, such as from drilling mud or formation water. O. C. Mullins, M. Hashem, H. Elshahawi, G. Fujisawa, C. Dong, S. Betancourt, T. Terabayashi, Petrophysics 46, 302 (2005).

Fluid density provides a means of fluid typing. Water has a density of 1.0 g/cm$^3$. Densities of liquid-rich hydrocarbons vary between 0.5 to 0.9 g/cm$^3$, and dry gas or condensate formations have a significantly lower density. The above values are understood to vary with reservoir pressure and temperature. Further, an understanding of the heterogeneity of the reservoir may require that densities be measured at several depths so that the compositional variation can be fully deduced. Such information can aid in identifying zones with the highest economic value; for example a dry gas may be preferred if the well is drilled in a gas field with existing infrastructure to handle gas transport through pipelines. Furthermore, for a given gas composition, the amount of standard cubic feet (SCF's) of gas producible is directly proportional to the density. Knowledge of the fluid density is essential for avoiding costly economic errors in applications such as, by non-limiting example, oilfield applications.

It is straight-forward to measure a liquid density at ambient pressure and temperature in a laboratory setting. Typically a flask of well-defined volume (volumetric flask) is filled with the fluid of interest and it is weighed on a scale. The density is obtained by dividing the fluidic mass by the known volume. Measurements at elevated pressure and temperature, however, require more sophisticated techniques. Gaseous fluids and heterogeneous liquids further complicate the measurement task. There are some known measurement methods employed for pressure/temperature density measurements, but they have limitations for downhole implementation.

For example, a known method includes using a resonating sensor such as a resonating tube densitometer and a Coriolis flow meter. However, such methods are not well-suited for subterranean applications. Firstly, the sizes of such flow meters in many cases are too large to fit in downhole tools such as, by non-limiting example, oilfield applications. Secondly, mud can be omnipresent at the beginning of a job (i.e., an oilfield application job), and it is unclear whether that mud can be completely cleaned from the two flow lines of the sensor. Thirdly, the method operates at pressures in the order of 1,000 psi, which makes such a method unusable at pressures much higher than 1,000 psi.

Furthermore, there are special fluid conditions that can present problems for resonating sensors in measuring fluid properties, such as density. For example, some of the problems with resonating sensors include inaccurate measurements of fluid properties, such as density, due to special fluid conditions, i.e., gaseous fluids, emulsions, non-Newtonian fluids, supercritical fluids or multiphase fluids.

Therefore, there is a need for a device, method, and system that can measure fluid properties such as density for oilfield applications and other industries that can overcome the above noted problems either above ground or in a subterranean environment.

SUMMARY

According to some embodiments of the disclosed subject matter, a device for measuring one or more properties of a fluid, including density, is disclosed. The device comprises a pressure housing having one or more windows formed in the pressure housing. The device includes a flow device arranged in the pressure housing for the fluid to flow through the flow device and one or more radiation sources mounted within the pressure housing approximate a first source window of the one or more windows that is configured to generate particles into the fluid. Finally, the device has one or more detectors supported by the pressure housing and positioned approximate a first detector window of the one or more window. The first detector window is located between the one or more detectors and the flow device. It is noted that the one or more detectors can be from a group consisting of one of a solid state detector, radiation detector, a scintillator detector or a gas detector, a solid state charged beta particle detector, a beta particle ionization detector, a wide band gap solid state detector, such as a diamond detector, or another radiation detecting device.

According to some aspects of the disclosed subject matter, the fluid can be from the group consisting of at least one liquid, at least one solid mixed with the at least one liquid, at least one gas or some combination thereof. Measurements can be made while the fluid temperature is one of at least −150 Celsius or greater, at least −50 Celsius or greater, at least 50 Celsius, at least 100 Celsius or at least 175 Celsius. The fluid can be flowing or not flowing through the flow device while measuring the one or more property of the fluid, which includes density. Further, the fluid may be a supercritical fluid such as carbon dioxide (CO2) that is in a supercritical condition which is approximate to a downhole application. The fluid can be one of an emulsified fluid, a drilling fluid or a multiphase fluid.

According to some other aspects of the disclosed subject matter, the one or more radiation sources may be from the group consisting of a beta particle source, a strontium source, a strontium 90 source or a positron source. The one or more radiation sources can produce beta particles within an energy range of 2 MeV to 3 MeV. The generated beta particles of the one or more radiation sources can be emitted through the first source window, into the flow device containing the fluid, out of the flow device, and through the first detector window to be detected by the one or more detector. At least one electronic device, such as a processor, is in communication with the one or more detectors for receiving a pulsed signal from the one or more detectors in one of a downhole environment, a reservoir, a borehole, inside a surface metering device or testing device. The one or more detectors may be from the group consisting of one of a solid state detector, a radiation detector, a scintillator detector, a gas detector, a solid state charged beta particle detector, a beta particle ionization detector, a wide band gap solid state detector, such as a diamond detector, or another radiation detecting device.

According to some other aspects of the disclosed subject matter, a wide band gap solid state detector may include one of a band gap of approximately 5.45 eV, an approximate density of 3.51 g/cm$^3$ or an approximate dimension of a 5 mm length by a 5 mm width by a 0.5 mm height. The wide band gap solid state detector may operate in a routine environment of temperatures approximately equal to and above one of 150 Celsius or 200 Celsius or more. The wide band gap detector is compatible for applications in one of a microelectromechanical system (MEMS), a nanoelectromechanical system (NEMS), a micromachine related device, a nano-tips based detector or a Field-emitting array based gas detector.

According to some other aspects of the disclosed subject matter, a nano-tips based gas radiation detector, or field-emission gas tube may also operate in a routine environment of temperatures as stated above or more. With a dimension of a few millimeter length, by a few millimeter width, and by a 0.5 mm height, the detector is also compatible for applications in one of a microelectromechanical system (MEMS), a nanoelectromechanical system (NEMS), or a micromachine related device. As compared with a solid-state detector, the nano-tips based gas detector may advantageously output read-out pulses with large amplitudes and detect lower energy beta particles passing through the fluidic device due to induced avalanches from the ionization.

According to some other aspects of the disclosed subject matter, the at least one electronic device, such as a processor, can be in communication with the one or more detectors for receiving a pulsed signal from the one or more detectors. The at least one electronic device processes the received pulsed signals to provide a capability to determine the one or more properties, including density, of the fluid. The determined density measurement of the fluid may be from the group consisting of one of a gaseous fluid density measurement, an emulsion fluid density measurement, a non-Newtonian fluid density measurement, a supercritical fluid density measurement or a multiphase fluid density measurement. The device is in communication with a processor and a mass density measuring device that measures a mass density of the fluid. The processor is capable of determining a fluidic hydrogen index from data received from the device and the mass density measuring device. The device can be in communication with a processor and a fluidic hydrogen index measuring device that measures a fluidic hydrogen index. The processor is capable of determining a fluidic mass density from data received from the device and the fluidic hydrogen index measuring device.

According to some other aspects of the disclosed subject matter, the pressure housing can be of a material from the group consisting of a stainless steel or one or more other materials and stainless steel. The pressure housing may include a source space with a source retainer that is in communication with the first source window to secure the one or more radiation sources. The pressure housing may include a detector space, detector shield, and a detector cap that is in communication with the first detector window to secure the one or more detector. The detector space may further include an elastomeric device. It is possible the one or more detectors are structured and arranged to be integral with the pressure housing. The pressure housing may be capable of withstanding pressures up to 30,000 psi or more and temperatures to 200 Celsius or more. The device can be designed to operate at pressures of one of 10 k psi or more, 15 k psi or more or 20 k psi or more. Further, the device may be designed to operate at temperatures of one of more than −150 Celsius, more than −50 Celsius, at least 50 Celsius, at least 100 Celsius or at least 150 Celsius. It is noted the device can be designed to operate at pressures within the flow device of one of at least 5 kpsi, at least 10 k psi or at least 20 kpsi.

According to some other aspects of the disclosed subject matter, a method comprises deploying the pressure housing, the radiation source, the detector, the first source window and first detector window downhole, wherein the fluid measurements are made downhole. Further, the one or more windows and flow device are made of a material having an approximate density of a combination of a glass and a peek material or a combination of the glass, the peek material, and another material. It is noted that a thickness of the first source window, a wall of the flow device, and the first detector window can be approximately equal. It is possible that a thickness of the first source window, a wall of the flow device approximate the first source window, the first detector window, and a wall of the flow device approximate the first detector window may also be approximately equal. Further, a first distance from the first source window to the wall of the flow device approximate the first source window can be approximately equal to a second distance from the first detector window to the wall of the flow device approximate the first detector window. Further still, the first source window and the first detector window of the one or more windows can have a thickness capable of allowing transmission of particles from the one or more particle sources within the pressure housing to the one or more detectors to allow for the particles to be detected by the one or more detector. It is possible the one or more detectors is from the group consisting of one of a solid state detector, a radiation detector, a scintillator detector, a gas detector, a solid state charged beta particle detector, a beta particle ionization detector, a wide band gap solid state detector, such as a diamond detector, or another radiation detecting device.

According to some other aspects of the disclosed subject matter, the flow device can be from the group consisting of a tube, a flowline, a channel, a pipe and a microfluidic channel that is integral with the pressure housing. Further, the flow device can have one of a thickness or a diameter ranging from approximately equal to or less than 0.5 mm. It is noted the flow device can have one of two or more thicknesses such as a first and a second thickness or two or more diameters such as a first and a second diameter. Further still, the one or more beta sources can have two or more beta sources and the one or more beta detectors have two or more beta detectors. It is possible a first beta source and a first beta detector can be arranged to measure a mixed fluid and a second beta source and a second beta detector are arranged to measure a gas. It is noted that the device may further comprise: (a) a first beta source of the two or beta sources that is located approximate the first diameter of the flow device and the first source window, and a first beta detector of the two or more beta detectors that is located approximate the first diameter of the flow device and the first detector window; and (b) a second beta source of the two or beta sources that is located approximate the second diameter of the flow device and a second source window, and a second beta detector of the two or more beta detectors that is located approximate the second diameter of the flow device and a second detector window. Further, the at least one electronic device can be in communication with the first detector and the second detector for receiving a first pulsed signal from the first detector and a second pulsed signal from the second detector. The at least one electronic device processes the received first and second pulsed signals to provide the capability to determine the one or more properties, including density, of the fluid. Further still, the device can be deployed downhole and the one or more radiation sources mounted within the pressure housing generate particles into the fluid within one of a downhole environment, a reservoir, or in a borehole.

According to another embodiment of the disclosed subject matter, an apparatus for measuring one or more properties of a fluid, including density, in a subterranean environment. The apparatus comprises a pressure housing to be deployed within the subterranean formation having one or more windows formed in the pressure housing capable of operating in routine pressures of at least 15 kpsi; a flow channel arranged in the pressure housing for the fluid to flow through the flow channel; one or more particle sources mounted within the pressure housing approximate a first source window of the one or more windows are configured to generate particles into the fluid within an energy range up to 3 MeV; and one or more detectors mounted within the pressure housing approximate a first detector window of the one or more windows, the first detector window located between the one or more detectors and the flow channel.

According to some other aspects of the disclosed subject matter, the fluid may be from the group consisting of a liquid, a liquid mixed with a solid, a gas, or some combination thereof. The fluid flows or does not flow through the flow channel while determining the one or more properties of the fluid that includes density. The one or more particle sources can be from the group consisting of a beta particle source, a strontium source, such as a strontium 90 source, or a positron source. The one or more detectors may be from, but not limited to, the group consisting of one of a solid state detector, a radiation detector, a scintillator detector, a gas detector, a solid state charged beta particle detector, a beta particle ionization detector, a wide band gap solid state detector, such as a diamond detector, or another radiation detecting device. Further, at least one electronic device, such as a processor, can be in communication with the one or more detector for receiving a pulsed signal from the one or more detector, the at least one electronic device processes the received pulsed signals to provide the capability to determine the one or more properties, including density, of the fluid. Further still, the flow channel can have one of a thickness or a diameter ranging from approximately equal to or less than 0.5 mm. It is possible the first source window and the first detector window of the one or more windows can have a thickness capable of allowing transmission of particles from the one or more particle sources within the pressure housing to the one or more detectors to allow for the particles to be detected by the one or more detectors. It is noted that a portion of the pressure housing approximate the first detector window can have a thickness sufficient to substantially attenuate the transmission of particles so that a linear resolution of the one or more particle detectors is increased.

According to some embodiments, a system for measuring one or more properties of a fluid, including density, in a reservoir environment. The system comprises a pressure housing to be deployed within the reservoir formation that has one or more windows formed in the pressure housing; a flow channel arranged in the pressure housing for the fluid to flow through the flow channel; one or more beta particle sources mounted within the pressure housing approximate a first source window of the one or more windows is configured to generate beta particles up to a energy of 3 MeV into the fluid; and one or more detectors mounted within the pressure housing approximate a first detector window of the one or more windows, the first detector window located between the one or more detectors and the flow channel.

According to some other aspects of the disclosed subject matter, the one or more beta particle sources can be a strontium source, such as a strontium 90 source.

According to some embodiments, a method for measuring one or more properties of a fluid including density in a subterranean environment. The method comprises deploying a pressure housing within the subterranean formation configured to operate at temperatures of at least 150 Celsius, the pressure housing includes one or more windows formed in the pressure housing; arranging a flow channel in the pressure housing for the fluid to flow through the flow channel; mounting one or more beta particle sources within the pressure housing approximate a first source window of the one or more windows configured to generate particles into the fluid; and mounting one or more wide band gap solid state detectors, such as a diamond detector, within the pressure housing approximate a first detector window of the one or more windows, the first detector window located between the one or more radiation detectors and the flow channel.

According to some other aspects of the disclosed subject matter, the wide band gap solid state detector can include one of a band gap of approximately 5.45 eV, an approximate density of 3.51 g/cm$^3$, an approximate dimension of 5 mm height by 5 mm length by 0.5 mm width, or some combination thereof.

According to some embodiments, a method for measuring one or more properties of a fluid, including density, in a downhole environment. The method comprises deploying a pressure housing within the subterranean formation having routine environment temperatures of equal to or more than 140 Celsius, the pressure housing includes one or more windows and a flow channel formed in the pressure housing, wherein the fluid channel is arranged for the fluid to flow through the flow channel; mounting one or more beta particle sources within the pressure housing approximate a first source window of the one or more windows that is configured to generate beta particles into the fluid; and mounting one or more solid state charged beta particle detectors within the pressure housing approximate a first detector window of the one or more windows, the first detector window located between the one or more solid state charged beta particle detectors and the flow channel.

According to some other aspects of the disclosed subject matter, the one or more solid state charged beta particle detectors can be one of a beta particle ionization detector or a wide band gap solid state detector, such as a diamond detector. Further, the wide band gap solid state detector can include one of a band gap of approximately 5.45 eV, an approximate density of 3.51 g/cm$^3$, or an approximate dimension of 5 mm height by 5 mm length by 0.5 mm width.

According to some other aspects of the disclosed subject matter, the fluidic channel or flowline can be geometrically wide or flat (the flow channel cross-section for example can be a few centimeters×a few millimeters) so that the flowing volume can be maintained high while the beta particle pass length is kept around a few millimeters. In such a geometrical arrangement, multiple Sr90 sources and multiple detectors can be implemented across the "flat" flowing channel, resulting in a high counting or measurement speed.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 4B illustrates a spectra of counting rate versus MCA channel for two different preamp cable lengths, where the location of the noise threshold is graphically shown and the channel number or energy corresponding to these points is what is referred to as the noise threshold, according to some embodiments;

DETAILED DESCRIPTION OF THE PREFERRED EMBODIMENTS

Figure 1:
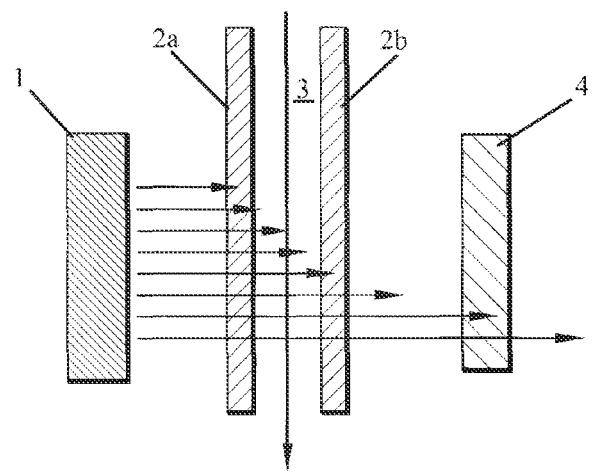
FIG. 1 illustrates the principle of a flow line densitometer which consists of a beta emitter, a flowline having a first wall and a second wall, fluid flowing through the flow line and a beta particle detector. The beta particle flux, as illustrated by the array of arrows, is attenuated by the flowline walls and by the fluid passing through the flowline, wherein the fluid density can be deduced from the beta particle flux changes, i.e., the counting rate changes in the detector, according to some embodiments.

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It is understood that various changes may be made in the function and arrangement of elements without departing from the spirit and scope of the subject matter disclosed in the application as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the subject matter disclosed in the application may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Furthermore, embodiments of the subject matter disclosed in the application may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

According to an embodiment, a device for measuring one or more properties of a fluid including density is disclosed. The device comprises a pressure housing having one or more windows formed in the pressure housing. The device includes a flow device arranged in the pressure housing for the fluid to flow through the flow device, and one or more radiation sources mounted within the pressure housing approximate a first source window of the one or more windows that is configured to generate particles into the fluid. Finally, the device has one or more detectors supported by the pressure housing and positioned approximate a first detector window of the one or more windows. The first detector window is located between the one or more detectors and the flow device. It is possible that the one or more detectors can be from the group consisting of one of a solid state detector, a radiation detector, a scintillator detector, a gas detector, a solid state charged beta particle detector, a beta particle ionization detector, a wide band gap solid state detector, such as a diamond detector, or another radiation detecting device.

Further, according to some embodiments, the devices, methods and related systems described for measuring one or more properties of a fluid, including density, include a pressure housing having one or more windows formed in the pressure housing, and a flow device arranged in the pressure housing for the fluid to flow through the flow device. Further, the devices, methods and related systems include a radiation source mounted within the pressure housing approximate a first source window of the one or more windows and configured to generate particles into the fluid. Also, the devices, methods and related systems include a detector supported by the pressure housing and positioned approximate a first detector window of the one or more windows. The first detector window is located between the detector and the flow device. The detector can be a solid state charged beta particle detector, such as a diamond detector, and the radiation source can be a beta particle source, such as a strontium 90 source.

The subject matter of the application includes, by non-limiting example, the technique for downhole fluid density measurement that involves no direct contact of the sensor with the fluid to be measured. In particular, using a detector to measure the density-dependent attenuation of beta particles. The density measured is a volumetric average of the fluid density situated between a source and the detector and as such is less dependent upon surface contamination (i.e. scale buildup or the like), a common problem for density measurements in the challenging subterranean environment, i.e., downhole.

It is contemplated that at least two implementations for such a measurement may include a macroscopic implementation and a microscopic implementation. The macroscopic implementation may have applications in conventional oilfield application tools where the beta path length through a flowline is about approximately a few millimeters. An example of microscopic implementation is a density measurement downstream of a microfluidic separator through a microfluidic channel of a diameter of approximately 0.5 mm or less.

FIG. 1 is a sketch that illustrates a flowline densitometer which consists of a beta emitter 1, a flow line having a first wall 2a and a second wall 2b, fluid 3 flowing through the flowline and a beta particle detector 4. The beta particle flux is illustrated by an array of arrows attenuated by the flow line walls 2a and 2b and by the fluid 3 passing through the flow line. The fluid density can be deduced from the beta particle flux changes, i.e., the counting rate changes in the detector 4. The interactions of fast electrons or beta particles with materials are discussed in the Knoll reference. See Glenn F. Knoll, Radiation Detection and Measurement, Third Edition, Chapter 2, John Wiley & Sons Inc., (2000). When beta particles pass through materials, the particles lose energy due to ionization, excitation, and bremsstrahlung. The first two, often referred to as "collisional losses," are dominant for beta particles with energies less than a few MeV. The "rate" of such energy losses or specific energy losses –dE/dx along a beta particle track can be factorized by the classical expression, which is known as the Bethe formula:

$$-\frac{dE}{dx} = \frac{2\pi e^4}{mv^2} * NZ * B \qquad \text{Eq. 1}$$

Where m is the electron mass, e the electron charge, and v the electron velocity. N and Z are the number density and the atomic number of the absorbing material atoms. B represents the Bethe formula for the collisional losses of fast electrons, and is related to electron velocity or energy and the average excitation potential and average ionization potential of the absorber, which is a constant for many common elements, compounds, and different materials for fast electrons. Thus, for electrons with a given energy (mono-energetic), the electrons can travel a certain distance in a given absorbing material. This distance is called the electron "range" and is reversely correlated to the electron number density in the material as shown by the NZ product in Eq. 1. The attenuation of beta particles emitted by a radioisotope source, because of the continuous distribution in their energy, differs significantly from the simple picture for mono-energetic electrons. The low energy beta particles are rapidly absorbed by a small thickness of the absorber material, so that the initial slope on the attenuation curve is greater. For the majority of beta spectra, the curve will have a near-exponential shape and is therefore nearly linear on the semilog plot. An "absorption co-efficient" $\mu$ is sometimes defined by:

$$\frac{I}{I_0} = e^{-\mu t} \qquad \text{Eq. 2}$$

where $I_0$ is the counting rate without absorber, I is the counting rate with absorber, and t is the absorber thickness. The co-efficient $\mu$ is directly proportional to the beta energy losses in the absorber material and convoluted by the continuous energy distribution of the beta particles emitted from a source with fixed-endpoint energy. Hence, the coefficient $\mu$ is directly related to the material density of the absorber. And the attenuation measurements can be used to extract the material density of the absorber.

Still referring to FIG. 1, the beta emitter may be one of a source, a radiation source, a beta particle source, a strontium source, a strontium 90 source, or a positron source. For the purposes of the claimed subject matter of the application, at least one embodiment, contemplates mounting the radiation source within a pressure housing 10 (see FIG. 3) approximate a first source window 11a within the pressure housing 10 that is configured to generate particles into the fluid 3 approximate the first wall 2a of the flowline. Further, the flow line may be one of a flow device, a tube, a flow line, a channel, a pipe, and a microfluidic channel that is integrated with the pressure housing 10. It is contemplated that the flow line may be separated from or integrated with the pressure housing 10 or partially separated and integrated.

Figure 2:
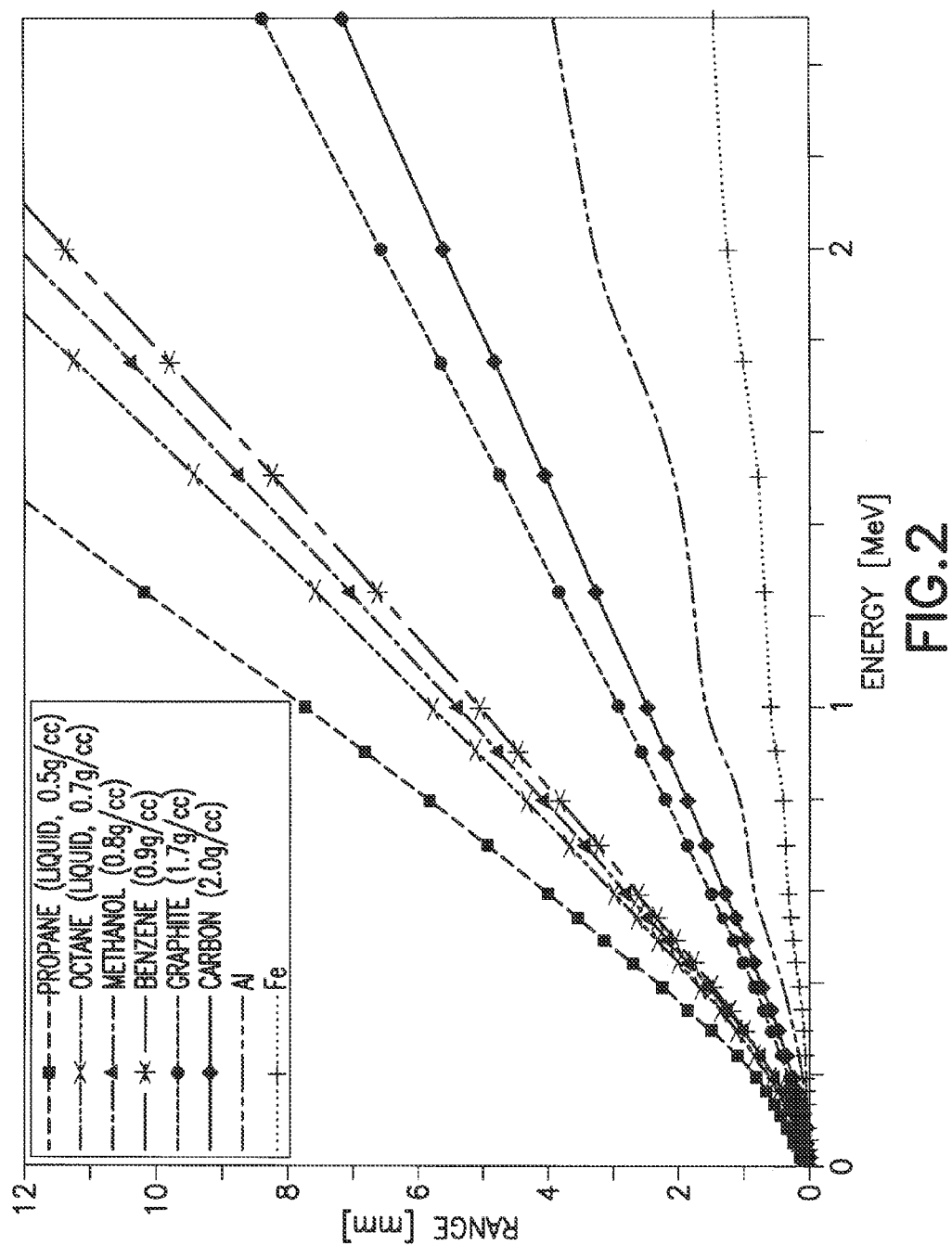
FIG. 2 illustrates a beta particle penetration distance as a function of its energy, according to some embodiments.

Still referring to FIG. 1, while it is possible that other sources may be used, for the purposes of the claimed subject matter disclosed in the application the source used may be a strontium 90 source. Strontium 90 provides many advantages, some of the advantages include, by non-limiting example, a high beta particle energy (maximum of 2.3 MeV) with a relatively smooth beta energy distribution and a relative long lifetime of 29 years. FIG. 2 illustrates a beta particle penetration distance as a function of its energy compiled with a computation program from NIST. See M. J. Berger, J. S. Coursey, M. A. Zucker and J. Chang, Stopping-Power and Range Tables for Electrons, Protons, and Helium Ions, NIST, Physics Laboratory, Ionizing Radiation Division, the databases and the computational programs: estar, pstar, and astar (http://www.nist.gov/phylab/data/star/).

A high energy allows the beta particles to penetrate through 1-10 mm of liquid, for example. As beta particles travel through material, the beta particles interact with shell electrons of atoms or molecules and produce ionization events, each time losing on the order of tens of electron volts of energy.

Still referring to FIG. 2, for example, a beta particle of energy 2 MeV can penetrate through one centimeter of 1 $g/cm^3$ liquid before losing its entire energy. Thus, sufficient energy is necessary for the particles to traverse both the flowline walls 2a and 2b and the fluid 3 of FIG. 1 and generate a readable pulse in the detector 4 (see FIG. 1). Therefore, for optimal sensitivity, the flowline diameter should be about a few millimeters for most liquids and the window walls 11a and 11b (or first and second source windows) have to be thin and made of low-density materials such as Peek (1.3 $g/cm^3$). For high-pressure applications, such thin window walls 11a and 11b (or first and second source windows) may require pressure compensation (see FIGS. 3A and 3B). For gaseous fluids (less dense than liquids), the flow line diameter can be enlarged or can be pressurized in a few mm flow line.

Still referring to FIG. 2, the penetration depth (or range) of betas as a function of their energies for a few fluids and solid materials are shown. The penetration ranges can be a guide in determining the optimal flow channel dimension for the types of fluids to be measured. Obviously, for less dense gas flows the dimension can be quite large (up to centimeters). However, it is noted that a 2 mm flow channel with thin windows 11a and 11b (or first and second source windows) facing both the source 1 and detector 4 will work for most fluids of interest including pressurized gases.

Figure 3A:
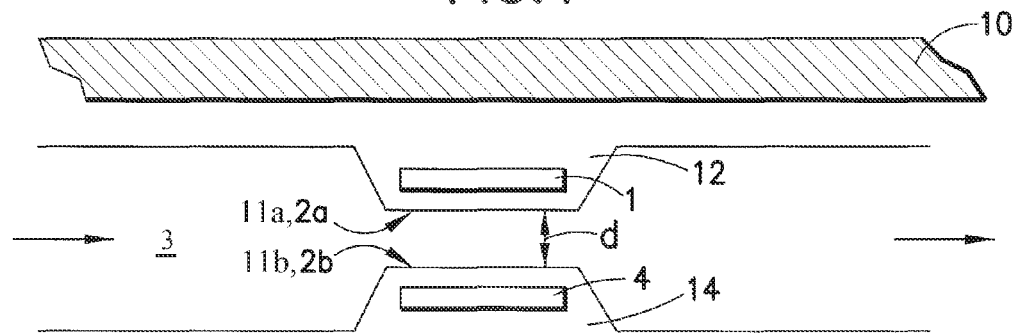
FIG. 3A illustrates a pressure housing that includes a flow device, a beta source, and a beta detector having a single pressure compensated set of chambers with one distance between the beta source and the beta detector, according to some embodiments.
Figure 3B:
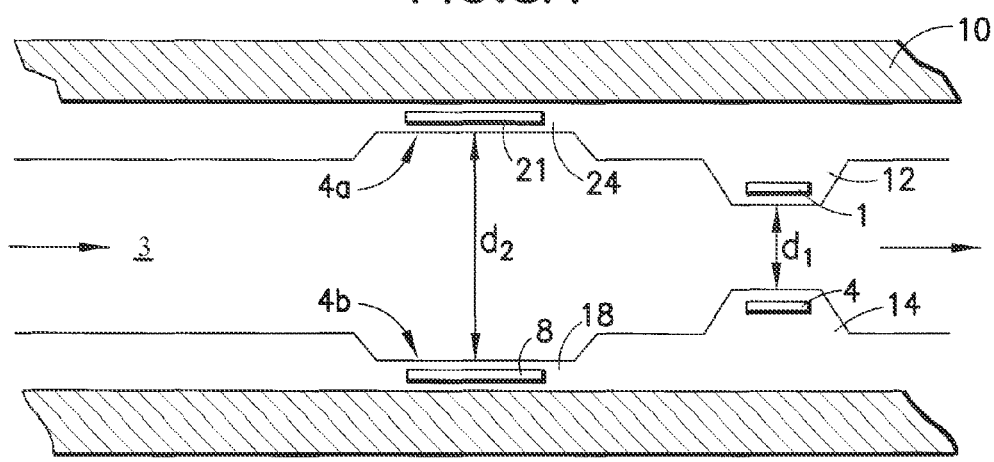
FIG. 3B illustrates a pressure housing that includes a flow device, having two beta sources and beta detectors, wherein each has a single pressure compensated set of chambers with a distance between the beta source and the beta detector, according to some embodiments.

Referring to FIG. 3A and FIG. 3B, FIG. 3A shows a pressure housing 10 having a source space 12 for the source 1, a flow line having walls 2a and 2b (or first 2a and second 2b source windows) with a distance (d), and a diamond detector 4, which is inside a detector space 14. The arrows (not numbered) indicate the direction of flow. It is noted, for example, it is possible that the flow line may have a 2 mm×10 mm cross-sectional area to fit a main flow line with a 5 mm diameter. It is also possible that the pressure housing 10 can be used in high pressure flow line applications that could include a pressurized system.

FIG. 3B shows a pressure housing 10 having a first source space 12 for a first beta source 1, a flow line having walls 2a and 2b (or first wall 2a and second wall 2b source windows) with a first distance ($d_1$), a first diamond detector 4, which is inside a first detector space 14. Also, FIG. 3B includes a second source space 24 for a second beta source 21, the flowline having walls 4a and 4b (or first wall 4a and second wall 4b source windows) with a second distance ($d_2$), and a second diamond detector 8, which is inside a second detector space 18. The arrows (not numbered) indicate the direction of flow. As noted above, for example, it is possible that the flow line may have a 2 mm×10 mm cross-sectional area to fit a main flow line with a 5 mm diameter. It is also possible that the pressure housing may be used in high pressure flow line applications that could include a pressurized system.

Still referring to FIGS. 3A and 3B, it is noted that low energy beta emitters may be used in a microfluidic version where flow line walls and the flow line are in a sub-millimeter range. The energy required for beta particles to penetrate a sub-millimeter material is relatively low.

Still referring to FIGS. 3A and 3B, it is possible that positron emitters, such as Na22, could work as well as beta emitters, although it is noted that most positron emitters emit low-energy positrons. Positrons can be similar to beta particles (electrons) except for their positive charges. For example, other than producing ionization, positrons will also interact with electrons to form positronium states and annihilate into a pair of photons. The thin solid-state detector is not sensitive to these photons and can still be used to detect penetrating positrons. It is possible that one can use a scintillator detector to detect photons from annihilation. Of which, by non-limiting example, those physical processes may lead to different applications. As noted above it is also possible that the one or more detectors can be one of a solid state detector, a radiation detector, a scintillator detector, a gas detector, a solid state charged beta particle detector, a beta particle ionization detector, a wide band gap solid state detector, such as a diamond detector, or another radiation detecting device.

Still referring to FIGS. 3A and 3B, mono-energetic beta emitters, such as Bi207, may also be used. Here one will need to use energy spectroscopy information from the detector and correlate the energy losses to the fluid density. It is noted, that this may put an additional burden on the read-out electronics.

Still referring to FIGS. 3A and 3B, beta particle emitters, producing betas with a continuous distribution of energy, such as Sr90, are ideal for this application. As shown in FIG. 2, beta particles with different energies penetrate different depths. The counting rate in the detector is directly correlated with the flow density. Therefore, the read-out electronics can be a simple counting circuit with a stable threshold. Energy spectroscopy information from the detector is not required.

Still referring to FIGS. 3A and 3B, the detector counting rate depends on the strength of the beta emitter and the flowline design. Based on the feasibility studies carried out in the lab, a Sr90 beta emitter with an activity in the range of 10-50 uCi is sufficient to give a precise density measurement in a second or in a few seconds with a 2 mm flow line. Certainly, one can change the source strength to adjust the measurement time.

Still referring to FIGS. 3A and 3B, in oil wells the ambient temperature is often above 130° C. A traditional silicon detector will have difficulty operating in such an extreme temperature environment. However, diamond detectors have shown a remarkable performance even beyond 200° C., thus, diamond detectors are ideal for downhole applications.

Still referring to FIGS. 3A and 3B, diamond detectors work in the same way as a silicon detector (or more generally a semiconductor detector). Semiconductor detectors are widely used for radiation detection, especially for charged particle detection. However, the diamond detector has one intrinsic advantage over semiconductor detectors due to its large band-gap, which makes the diamond detector ideal for high-temperature applications, i.e., downhole applications.

Figure 4A:
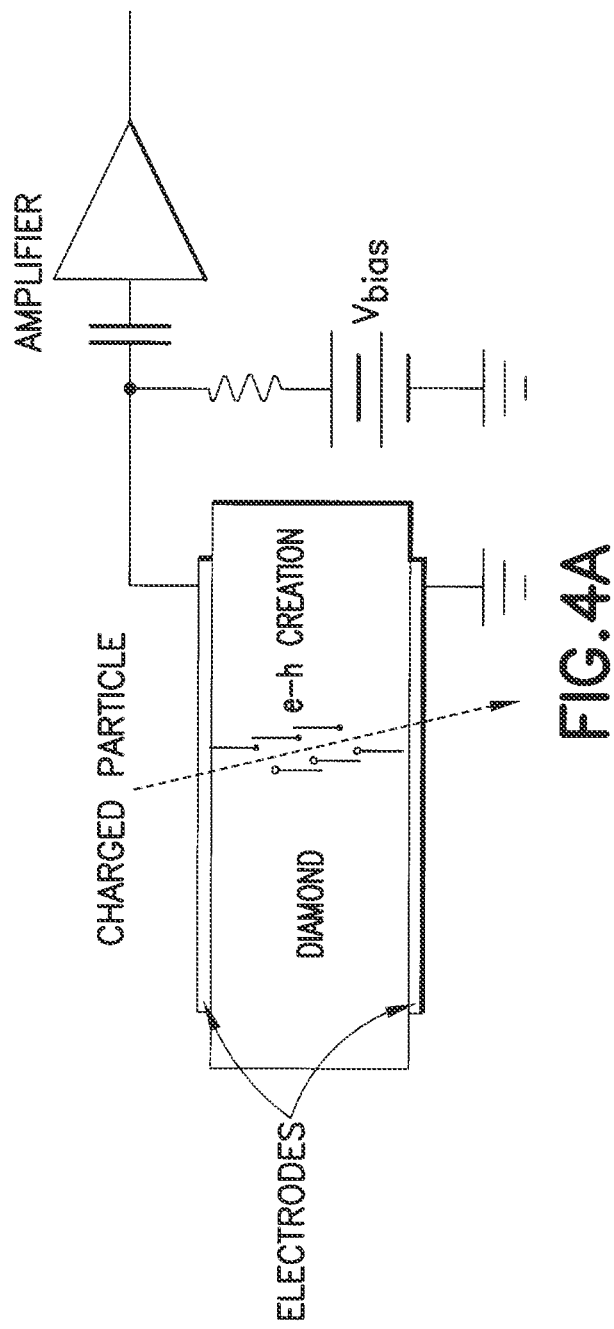
FIG. 4A illustrates detection of charged particles using a diamond detector, according to some embodiments.

FIGS. 4A and 4B, FIG. 4A is a sketch that shows detection of charged particles using a diamond detector. The working principles of a diamond or a semiconductor detector are quite similar. Radiation is measured by means of the number of charge carriers set free by the radiation in the detector volume between two electrodes. Ionizing radiation produces free electrons and holes, namely, a number of electrons are transferred from the valence band to the conduction band, and an equal number of holes are created in the valence band. The number of electron-hole pairs is proportional to the energy deposited by the radiation in the detector volume. Under the influence of an electric field, electrons and holes travel to the electrodes and produce an electrical pulse that is measured with a charge-sensitive amplifier (often called "pre-amplifier"). As the amount of energy required for creating an electron-hole pair is known, and is independent of the energy of the incident radiation, the number of electron-hole pairs produced is proportional to the energy of the incident radiation.

TABLE 1

Band Gaps and Density Properties for Several Materials.

|  | Silicon | Silicon-carbide | Diamond |
| --- | --- | --- | --- |
| Band gap (eV) | 1.11 | 2.86 | 5.45 |
| Density (g/cm$^3$) | 2.33 | 3.22 | 3.51 |

Still referring to FIG. 4A, for comparison, the band gaps and densities of a few materials are listed in Table 1 above. The very large band gap of diamond detectors results in a very small leakage current when biased with an electric field, even at more than 200° C. This characteristic makes diamond detectors ideal for oil-field or any other high-temperature applications.

FIG. 4B illustrates a typical spectra of beta particles from a Sr90 source as read out from a diamond detector in the present setup for two different preamp cable lengths. The read-outs from the amplifiers were analysed by a pulse height analyser (PHA) and plotted as a function of a MCA (multi-channel analyser) channel number. The location of the noise threshold is graphically shown. The channel number or energy corresponding to these points is what is referred to as the noise threshold. In particular, the noise was drastically reduced and more stability was maintained by installing an uninterruptable power supply (UPS) in the testing laboratory. The signal going from the detector to the preamp is only a few fC of charge collected in ~10 ns and is very susceptible to interference. Normally preamplifiers are placed very close to the detector to minimize the RF pickup and the capacitance of the cable. However, for an actual implementation of this device in a down-hole application, it may be desirable to have a longer cable between the detector and the preamp. The noise picked up by the cable between the detector and the preamp is a function of the cable length, so the question exists of how long of a cable can be tolerated. The data show that a reasonable length of cable can be applied without an interference to the measurements in this setup.

Some additional advantages of the diamond detector, by non-limiting example, include: (1) the detector has a small size, for example, a 5×5×0.5 mm detector, which is ideal for applications where there is little space (i.e., in a logging while drilling applications, especially for small borehole sizes), (2) the detector is compatible for applications in microelectromechanical systems (MEMS), nanoelectromechanical systems (NEMS) and micromachine related devices; (3) the detector is mechanically strong; (4) the detector is chemically stable even at high temperatures; (5) the detector is resistant to radiation damages; (6) the detector has excellent linearity and provides stability when used as a radiation detector, which makes it ideal for high-radiation and hostile environments applications; (7) the detector is easy to use, it needs approximate 200-500 V/cm bias; (8) the detector has a fast charge collection (~10 ns); (9) the detector has a good energy resolution for stopping alpha particles and beta particles (~4%); (10) the detector has a large signal comparable to silicon detectors; and (11) the detector has a very low leakage current (<pA).

It is noted that one of the alternatives to diamond detectors is to use a Silicon Carbide detector instead of a diamond detector, given the fact that SiC does have a relative large band gap as shown in Table 1 above.

Some other additional advantages of diamond detectors relevant to the claimed subject matter of the application include the ability of diamond detectors to make accurate measurements under subterranean environment conditions, such as downhole environment conditions. For example, at least one advantage over that of known resonating sensors is a diamond detector's ability to make accurate measurements of properties of fluids, such as density, when measuring fluids under special fluid conditions. Special fluid conditions, as noted above, include gaseous fluids, emulsions, non-Newtonian fluids, supercritical fluids, or multiphase fluids.

A special fluid condition such as a gaseous fluid presents problems for known resonating sensors when trying to measure fluid properties of fluids, such as density. For example, trying to get an accurate density measurement of any low density fluid, such as dry methane or condensates with low carbon number, is difficult for any technique, especially for a well-known resonating sensor. After the initial cleaning of a flow line of the resonating sensor, as well as any immersed sensor, it is almost assured that the resonating sensor will be coated with mud. While one can remove particulates and mud with a miscible fluid, such as oil directly from the formation, it is difficult to remove such residues with a gas stream. The analogy that is typically made is that one cannot wash oily hands with just a blast of air. Rather, one needs a fluid that is miscible and can dissolve away the coated particulates and solids. A residual thin layer of mud will dramatically reduce the accuracy of the measurement. On the other hand, the claimed subject matter of the application overcomes the above problems and is able to make accurate measurements of the properties of the fluid, such as density, by making a volumetric measurement through a fluid flow line which results in the measurement being less sensitive to such contamination.

Another example of a special fluid condition, such as emulsions, presents problems for the known resonator sensor when making density measurements. Oil/water emulsions are common in wells throughout the world. They may result from water breakthrough during a sampling job or from the shearing action of drilling when using water-based mud. The measurement of emulsions with a known resonating sensor is particularly challenging due to wetting effects. Typically, one fluid prefers to wet the sensor tip and thus provides a biased measurement. On the other hand, the claimed subject matter of the application overcomes the above problems and is able to make accurate measurements of properties of fluid, such as density by making a volumetric measurement that is largely insensitive to wetting.

Another example of special fluid conditions may include non-Newtonian fluids, which also present a significant challenge for resonating sensors. The shear rate of a resonating sensor immersed in fluid is maximum at its surface and decreases with distance, dictating that the shear rate is non-uniform throughout the interrogation volume. If the shear rate is non-uniform, then for a non-Newtonian fluid the shear stress will be non-uniform as well, producing a viscosity measurement that is certainly not representative of the zero shear rate viscosity. A preponderance of fluids experienced downhole appears to be shear-thinning, and measurements with a resonating sensor typically read low. A low accuracy measurement of the fluid viscosity with a resonating sensor that simultaneously measures fluid density often invalidates the interpretation and leads to incorrect density measurements. Again, a density measurement that did not involve resonance such as described in claimed subject matter of the application does not have this problem.

Another example of special fluid conditions may include supercritical fluids or multiphase fluids which also present significant challenges for resonating sensors. Supercritical fluid can be any substance at a temperature and pressure above its thermodynamic critical point. It can diffuse through solids like a gas, and dissolve materials like a liquid. There is no surface tension in a supercritical fluid as there is no liquid/gas phase boundary. Additionally, all supercritical fluids are completely miscible with each other. In general terms, supercritical fluids have properties between those of a gas and a liquid. However, close to the critical point, small changes in pressure or temperature result in large changes in density and viscosity, allowing many properties to be altered. Thus, these characteristics present enormous challenges for resonating sensors. Further, carbon dioxide is usually in supercritical form under most downhole conditions.

Since resonating sensors measure fluid properties in a local volume or a small surface area, multiphase fluids such as a liquid with gas bulbs will present another challenge. On the other hand, a nuclear volumetric measurement described here is insensitive to the apparent forms of fluids regardless whether they are in supercritical forms or multiphase.

Figure 5:
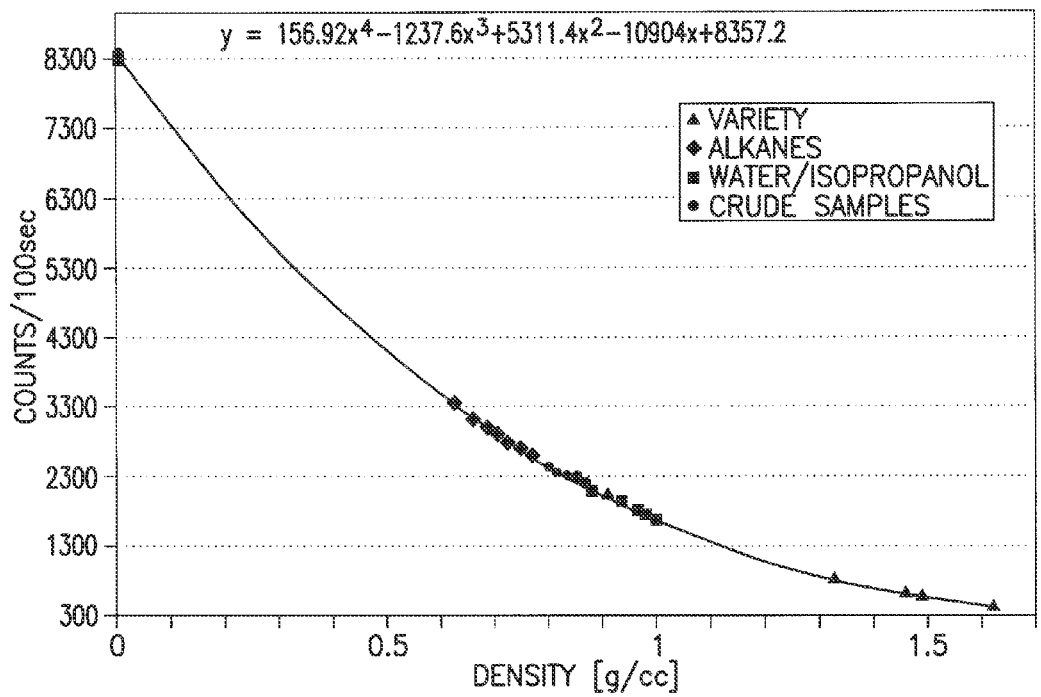
FIG. 5 is a plot illustrating beta particle counts in the detector as a function of the fluid density, wherein the trendline is a polynomial fit of all data except the crude samples, according to some embodiments.

FIG. 5 is a plot illustrating the beta particle counts in the detector as a function of the fluid density, wherein the trendline is a polynomial fit of all data except the crude samples. Further, the fluidic density measurements were carried out with a test setup in a lab to demonstrate the feasibility. The liquid samples include standard alkanes (C4 to C14), benzene, toluene, mixtures of benzene and toluene, water, isopropanol, mixtures of water and isopropanol, acetone, chloride hydrocarbon fluids, a few crude samples, and a few emulsified fluids were made in the lab with S20 and Hexadecane oils mixed with water. The following disclosure shows results for the above mentioned conventional fluids, leaving emulsified and supercritical fluids elsewhere. Note that the measurements were performed with a 1 uCi Sr90 source and a smaller version of a diamond detector, which resulted in a longer counting time.

Still referring to FIG. 5, FIG. 5 shows detector counts versus densities for most of the samples. Those measurements were accumulated over a couple of months. For each group of samples, repeated measurements were made with the empty flow-channel, or filled with hexane, and occasionally with hexadecane. The data show excellent repeatability and no normalization was needed. Furthermore, it is noted that a simple $4^{th}$ order polynomial fits the data very well.

Figure 6:
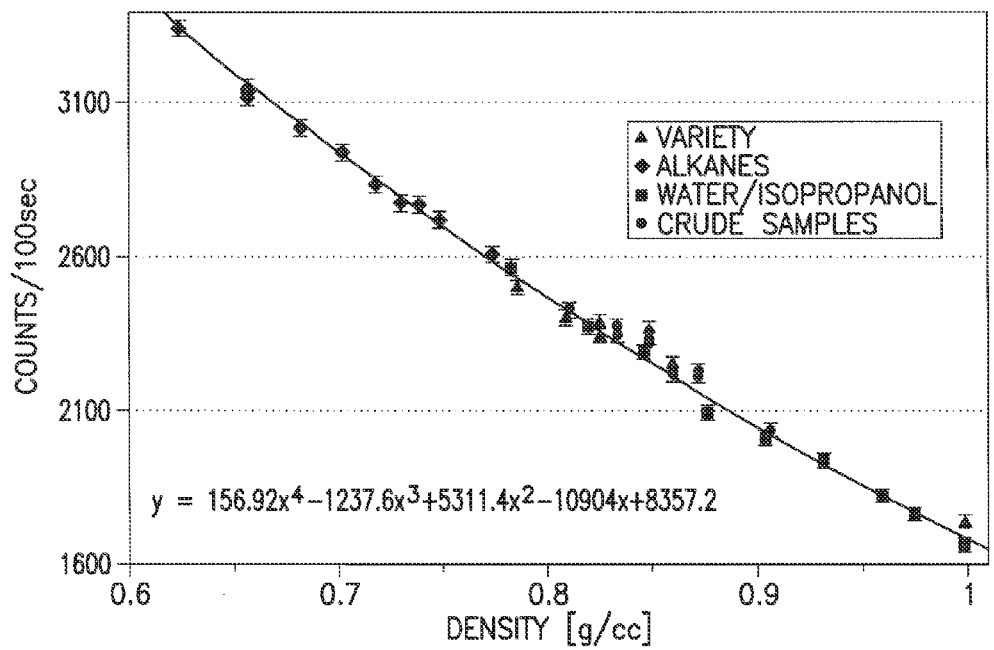
FIG. 6 is similar to FIG. 5, but includes only data in the density region from 0.6 to 1.0 g/cc, according to some embodiments.

FIG. 6 is similar to FIG. 5, but shows only data in the density region from 0.6 to 1.0 g/cc. In particular, FIG. 6 shows a zoom in view of the data in the density range from 0.6 to 1.0 g/cc. The statistical errors become visible in the present setup with a 1 uCi Sr90 source and a smaller version of the diamond detector.

Figure 7:
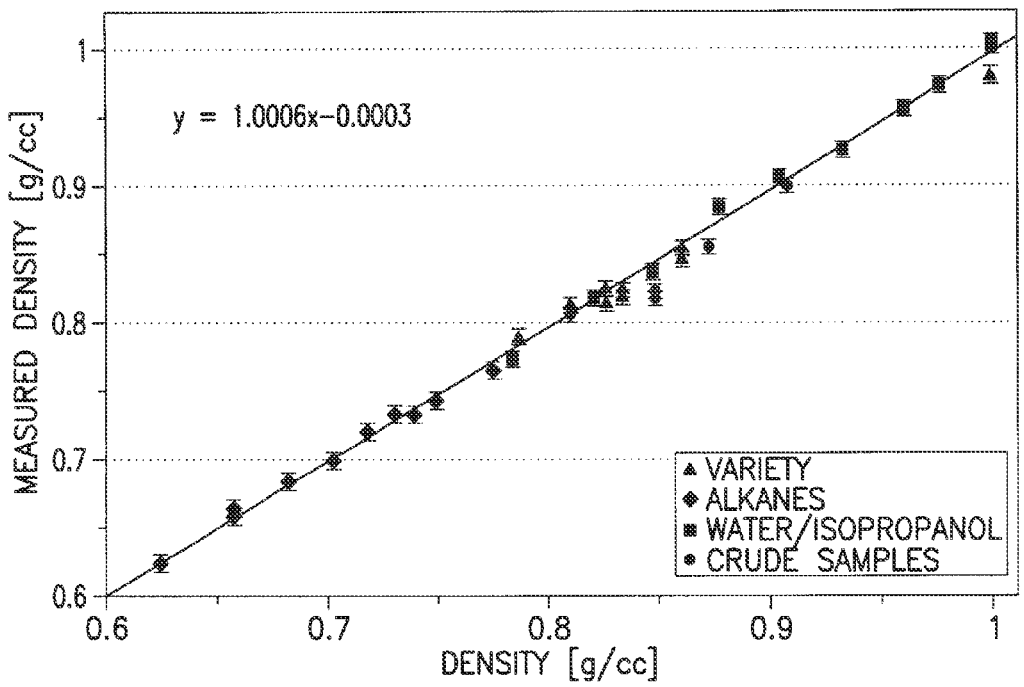
FIG. 7 illustrates a plot of measured density versus true density, wherein the line is a fit, according to some embodiments.

FIG. 7 illustrates measured density as a function of true density. The line is a fit. Also, one can invert the polynomial fit of the beta particle counts as a function of density to obtain the densities from the counts—the "measured" densities. FIG. 7 shows the results of the measured density as a function of the true density. The straight line fit reveals an excellent 1-to-1 ratio.

Figure 8:
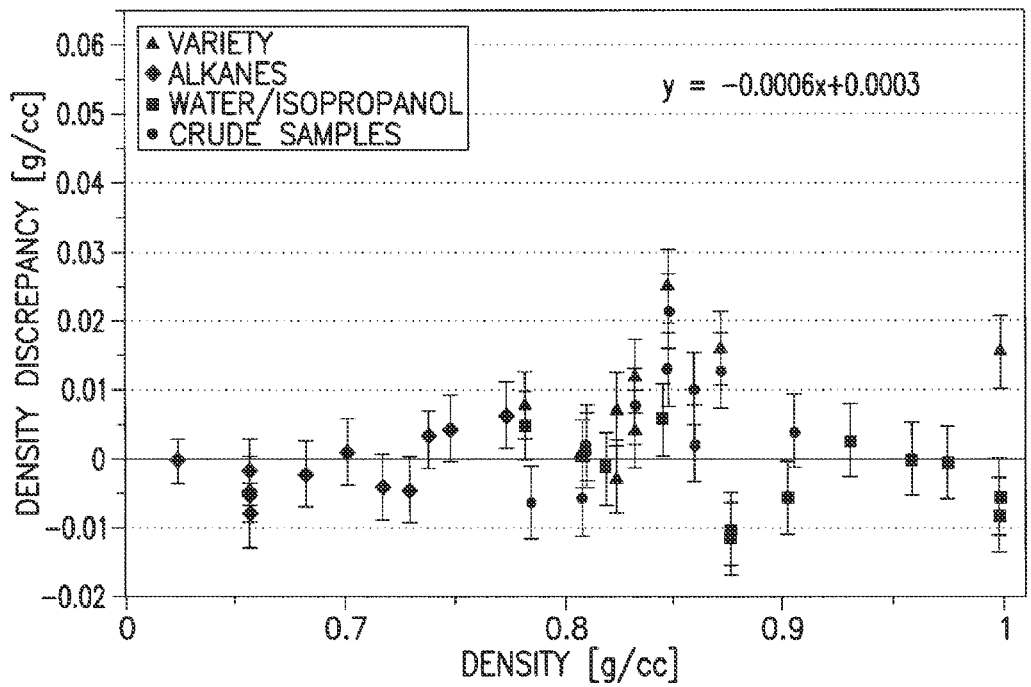
FIG. 8 illustrates a plot of the discrepancy between measured density and true density as a function of the true density, wherein the line is a fit, according to some embodiments.

FIG. 8 illustrates the discrepancy between the measured and true density as a function of the true density. The line is a fit. It is noted that the density discrepancy (the difference between the true density and the measured density) is shown in FIG. 8 as a function of density. The distribution is quite flat as a function of density, consistent with statistical errors.

From the data, one can be confident that the measurements are achieved with a 0.01 g/cc or better accuracy.

Figure 9:
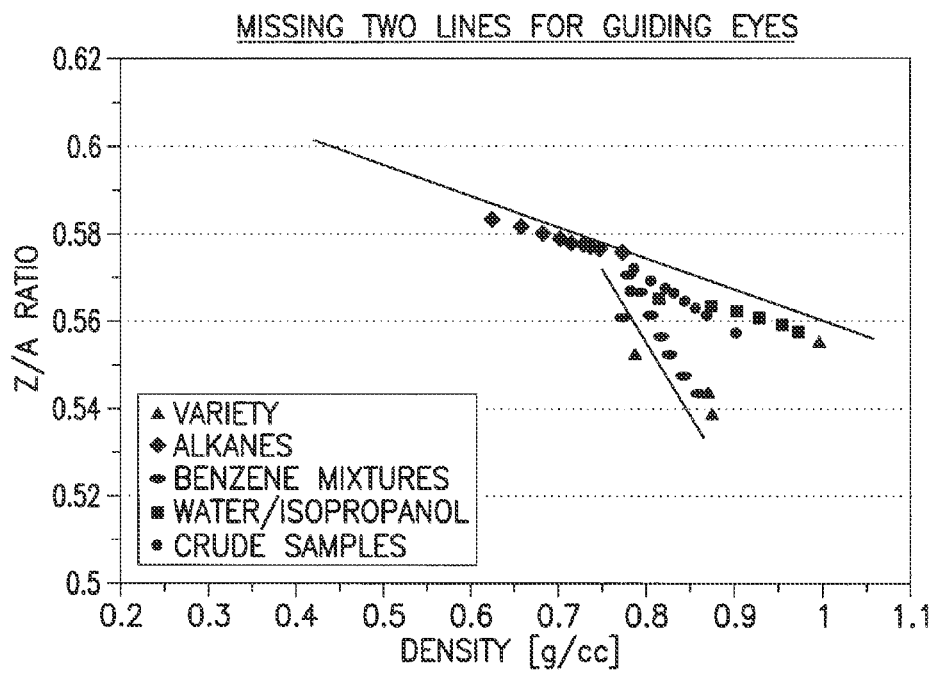
FIG. 9 illustrates a plot of the Z/A ratios of fluidic samples used in the measurements, wherein the Z/A ratio is defined by the atomic number "Z" and the atomic mass "A" for all the elements. The samples include alkanes, crude oils, and water/isopropanol mixtures that form a main trend line, while the other samples, those of acetone, benzene, toluene and their mixtures (benzene/hexadecane or toluene/hexane) form another branch, according to some embodiments.

FIG. 9 illustrates a plot of the Z/A ratios of fluidic samples used in the measurements, wherein the Z/A ratio is defined by the atomic number "Z" and the atomic mass number "A." In order to study the effects of aromatics, the density dependence of Z/A ratios was investigated using acetone, benzene, toluene, and their mixtures. Those fluids normally do not exist down hole or exist only in a very small percentage in crude oils. They have different Z/A ratios as compared with the rest of the samples. FIG. 9 shows Z/A for all the fluids studied. The samples of alkanes, crude oils, and water/isopropanol mixtures form a main trend line, while those of acetone, benzene, toluene and their mixtures (benzene/hexadecane or toluene/hexane) form another branch.

Still referring to FIG. 9, the Z/A ratios can be computed if the fluids compositions are known. One of the methods for determining the Z/A ratios is to determine fluidic compositions by using optical measurements, such as a downhole fluidic analysis device (DFA). Z/A ratios can also be measured by using the hydrogen index obtained from the NMR fluidic analysis. The Hydrogen index ($\omega_H$) is related to the Z/A ratio in a simple way:

$$Z/A = (1+\omega_H)/2. \quad \text{Eq. 3}$$

Figure 10:
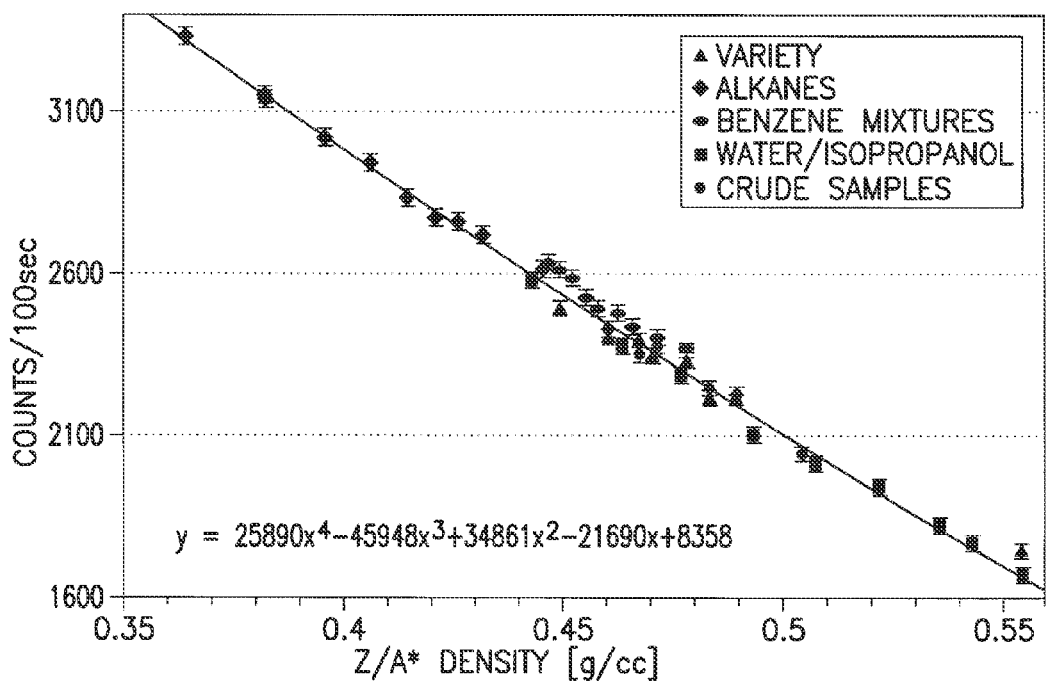
FIG. 10 is a plot showing counting rates as a function of the product of the Z/A ratios and densities, according to some embodiments.
Figure 11:
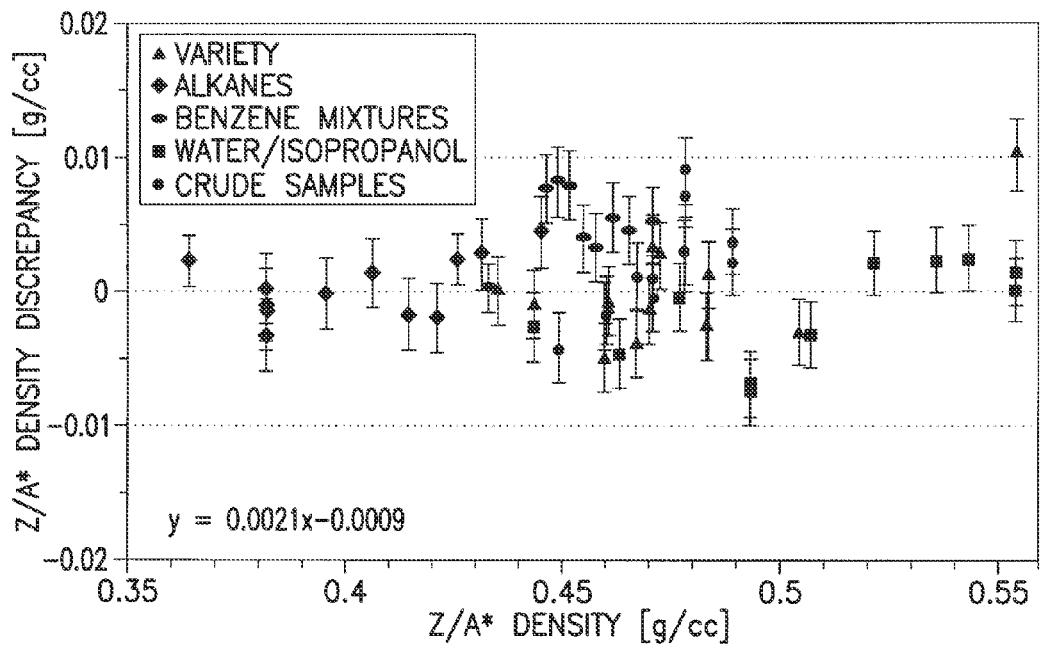
FIG. 11 is a plot showing the discrepancy between true and measured Z/A*Density as a function of the true Z/A*Density, which is often defined as the "electron density", according to some embodiments.

Referring to FIG. 10 and FIG. 11, FIG. 10 is a plot showing counting rates as a function of the product of the Z/A ratios and densities. The product of Z/A and density (often called mass density—$\rho_m$) can be defined as the electron density ($\rho_e$):

$$\rho_e = Z^*N/N_0 = Z/A^*\rho_m \quad \text{Eq. 4}$$

where $N/N_0$ is the number density of the material with $N_0$ the Avogadro's number.

FIG. 11 is a plot showing the discrepancy between true and measured electron density as a function of the electron density.

Still referring to FIGS. 10 and 11, the data in FIG. 5 includes only fluids that fall on the main Z/A trend line. For fluids belonging to the branch Z/A line, the counting rates will deviate from the main fit line and form similar branches in counting rates or measured density plots. A simple way to correct for the deviation is to plot everything as a function of the product of Z/A ratio and density (Z/A*density) (i.e., the electron density), instead of mass density. This can be seen in FIG. 10, one fit line can describe all the data points for counting rates regardless of the fluid types. This demonstrates that the attenuation of beta particle flux in the flowline is through ionization and is directly proportional to the electron density in the flow channel. Using the fit for counting rates, one can obtain "measured" electron densities. The discrepancy between the true and measured electron density for all the fluid samples are shown in FIG. 11. Again, the figure illustrates that it is possible to achieve a precision of 0.01 g/cc for fluid density with this technique.

Still referring to FIGS. 10 and 11, an important note here is that one can apply this downhole real-time measurement in two ways. As mentioned above, the Z/A ratio of flow can be obtained from the downhole fluidic analysis device (DFA) or NMR measurements. Combining with the method described herein, one can have a precise flow density measurement. Or, if one combines this method with another "true" mass density device, such as the in situ density device from Schlumberger down-hole fluidic analysis, which provides density measurements with a vibrating rod, one can immediately obtain the hydrogen index for the flow, as shown in Equation 4. Both of these may be advantageous in cases where other measurements are not practical or feasible.

Figure 12:
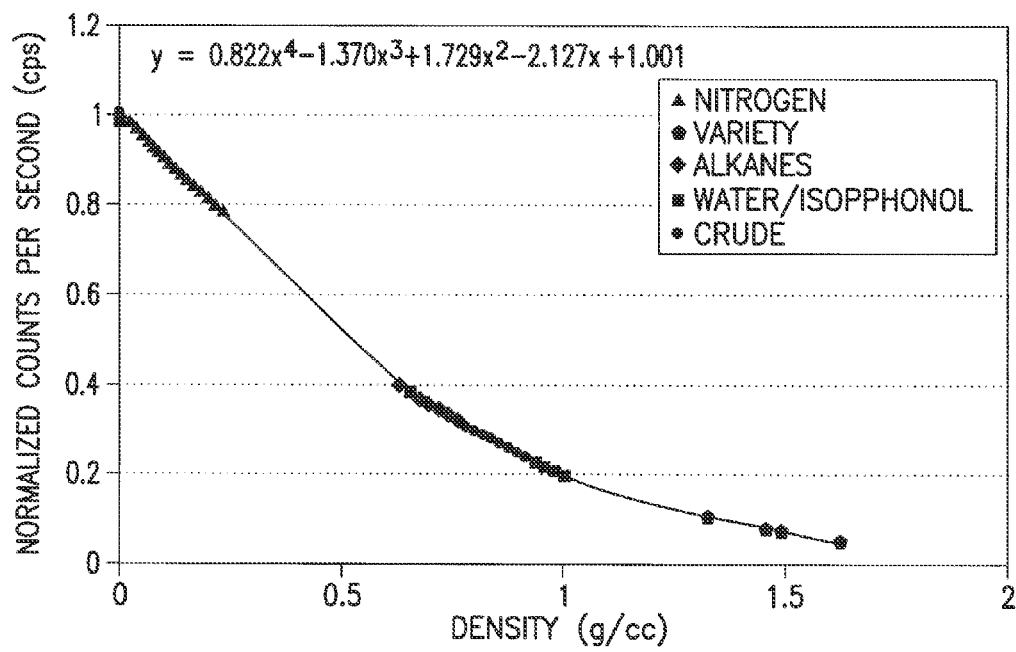
FIG. 12 illustrates pressurized nitrogen gas data plotted with previously taken liquid data versus density, normalized to an empty channel, according to some embodiments.
Figure 13:
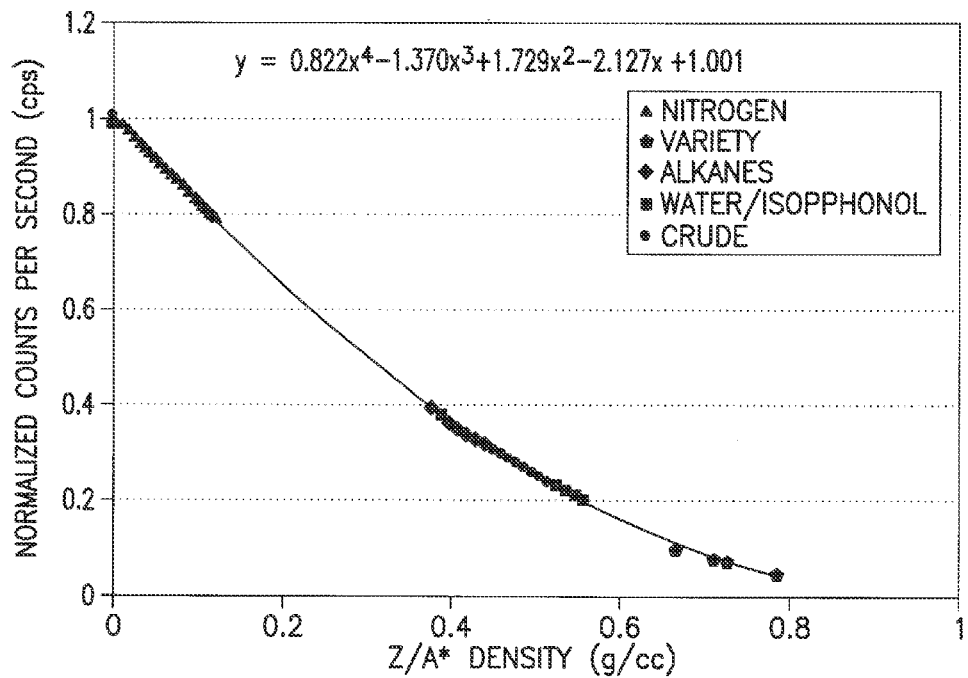
FIG. 13 illustrates a plot of normalized pressurized nitrogen gas data plotted with previously taken liquid data versus Z/A*Density to negate the effects of varying hydrogen indices of the materials, according to some embodiments.

FIGS. 12 and 13 show measurements with pressurized nitrogen gas. FIG. 12 illustrates nitrogen data plotted with previously taken liquid data versus density normalized to an empty channel. FIG. 13 illustrates normalized nitrogen data plotted with previously taken liquid data versus Z/A*Density to negate the effects of varying hydrogen indices of the materials. The two data sets are normalized to the empty channels filled with air at atmospheric pressure. Every data set has empty channel filled with air at atmospheric pressure to demonstrate repeatability at different times when data were taken. This normalization is necessary because the pressurized device design has approximately a much higher counting rate than the device used for previous liquid measurements due to a stronger Sr90 source and a bigger diamond detector.

Figure 14:
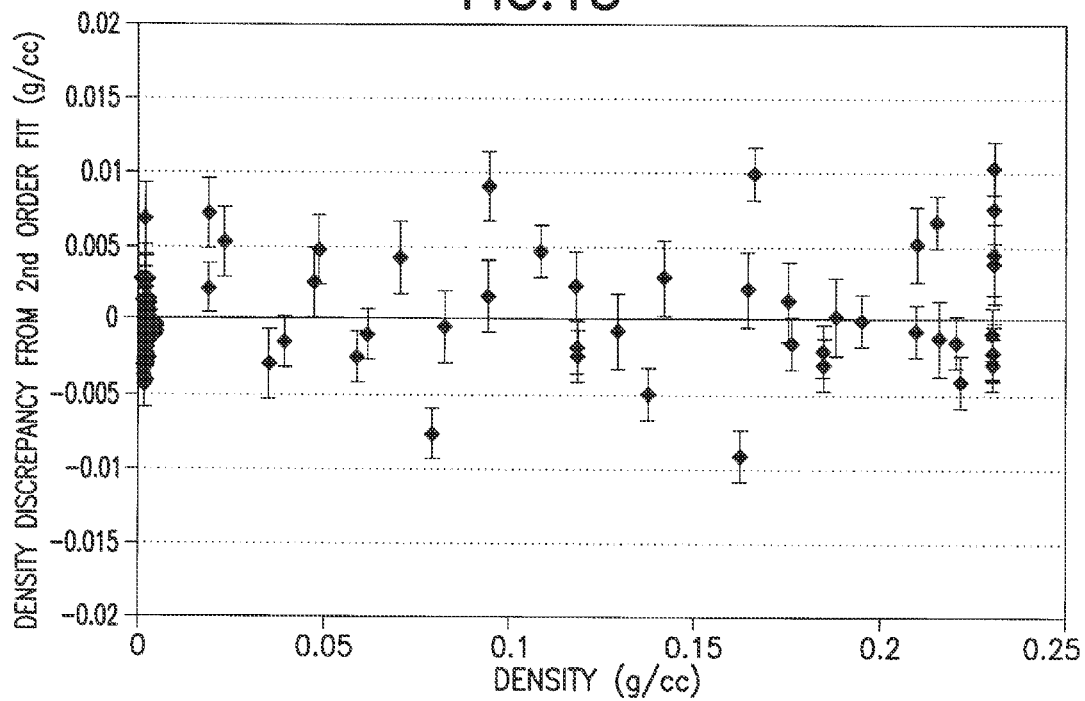
FIG. 14 illustrates a plot of density discrepancy for a second order fit as a function of density for repeated pressure cycles during nitrogen gas measurements, according to some embodiments.

FIG. 14 illustrates density discrepancy for the second order fit as a function of density for nitrogen measurements with repeated pressure cycles. The pressure cycles were found that most of the data falls within +/−0.005 g/cc of the second order trend line.

As noted above, it is contemplated that at least two implementations for such a measurement may include a macroscopic implementation, as discussed above, and a microscopic implementation. The microscopic implementation includes a density measurement downstream of a microfluidic separator through a microfluidic channel of a diameter of approximately 0.5 mm or less.

Whereas many alterations and modifications of the present disclosure will no doubt become apparent to a person of ordinary skill in the art after having read the foregoing description, it is to be understood that the particular embodiments shown and described by way of illustration are in no way intended to be considered limiting. Further, the disclosure has been described with reference to particular preferred embodiments, but variations within the spirit and scope of the disclosure will occur to those skilled in the art. It is noted that the foregoing examples have been provided merely for the purpose of explanation and are in no way to be construed as limiting of the present disclosure. While the present disclosure has been described with reference to exemplary embodiments, it is understood that the words, which have been used herein, are words of description and illustration, rather than words of limitation. Changes may be made, within the purview of the appended claims, as presently stated and as amended, without departing from the scope and spirit of the present disclosure in its aspects. Although the present disclosure has been described herein with reference to particular means, materials and embodiments, the present disclosure is not intended to be limited to the particulars disclosed herein; rather, the present disclosure extends to all functionally equivalent structures, methods and uses, such as are within the scope of the appended claims.

What is claimed is:

1. A device for measuring at least one property of a fluid, wherein the at least one property includes density, the device comprising:
   a pressure housing comprising:
      at least one beta particle source;
      at least one beta particle detector;
      at least one pressure compensated chamber comprising at least one of the beta particle source and the beta particle detector;
      a flow line for containing the fluid; and
      at least one source window and at least one detector window, wherein the beta particle source is configured to generate beta particles that pass through the source window, into the flow line containing the fluid, through the detector window, and are detected by the beta particle detector.

2. The device of claim 1, wherein the fluid is selected from the group consisting of:
   at least one liquid,
   at least one solid mixed with the at least one liquid,
   at least one gas, and
   some combination thereof.

3. The device of claim 2, wherein the fluid flows through the flow line while the at least one fluid property is measured.

4. The device of claim 2, wherein the fluid is a supercritical fluid.

5. The device of claim 2, wherein the fluid is selected from the group consisting of:
   an emulsified fluid,
   a drilling fluid, and
   a multiphase fluid.

6. The device of claim 1, wherein the beta particle source produces beta particles within an energy range of 1 MeV to 3 MeV.

7. The device of claim 1, wherein the beta particle detector is configured to operate at temperatures of at least 150 Celsius.

8. The device of claim 1, wherein the beta particle detector is compatible for applications in one of a microelectromechanical system (MEMS), a nanoelectromechanical system (NEMS), a micromachine related device, a nano-tips based detector, or a Field-emitting array based gas detector.

9. The device of claim 1, wherein a processor is in communication with the beta particle detector, the processor receives a pulsed signal from the beta particle detector, the processor processes the received pulsed signals, and the processor determines the at least one property of the fluid.

10. The device of claim 9, wherein the at least one property of the fluid is selected from the group consisting of:
    a gaseous fluid density measurement,
    an emulsion fluid density measurement,
    a non-Newtonian fluid density measurement,
    a supercritical fluid density measurement, and
    a multiphase fluid density measurement.

11. The device of claim 1, wherein the device is in communication with a processor and a mass density measuring device that measures a mass density of the fluid and the processor is configured to determine a fluidic hydrogen index from data received from the device and the mass density measuring device.

12. The device of claim 1, wherein the device is in communication with a processor and a fluidic hydrogen index measuring device that measures a fluidic hydrogen index and the processor is configured to determine a fluidic mass density from data received from the device and the fluidic hydrogen index measuring device.

13. The device of claim 1, wherein the pressure housing comprises stainless steel.

14. The device of claim 1, wherein the beta particle detector is structured and arranged to be integral with the pressure housing.

15. The device of claim 1, wherein the pressure housing is capable of withstanding pressures up to 30,000 psi or more and temperatures of 200 Celsius or more.

16. The device of claim 1, wherein the device is designed to operate at temperatures of at least 150 Celsius.

17. The device of claim 1, wherein the flow line is configured to withstand pressures within the flow line of at least 5 kpsi.

18. The device of claim 1, wherein the flow line comprises a combination of a glass material and a peek material.

19. The device of claim 1, wherein a thickness of the source window, a wall of the flow line, and the detector window are approximately equal.

20. The device of claim 1, wherein the source window is a part of a wall of the flow line and the detector window is a part of a wall of the flow line.

21. The device of claim 1, wherein the source window and the detector window have a thickness selected to allow transmission of beta particles from the beta particle source to the beta particle detector and to allow the particles to be detected by the beta particle detector.

22. The device of claim 1, wherein the flow line is selected from the group consisting of:
 a tube,
 a channel,
 a pipe, and
 a microfluidic channel that is integral with the pressure housing.

23. The device of claim 1, wherein the flow line has diameter ranging from approximately 0.5 mm to approximately 5 cm.

24. The device of claim 1, wherein the flow line has two or more diameters.

25. The device of claim 24, wherein the at least one beta particle source includes a first beta particle source and a second beta particle source, and the at least one beta particle detector includes a first beta particle detector and a second beta particle detector.

26. The device of claim 25, wherein the first beta particle source and the first beta particle detector are arranged to measure a mixed fluid and the second beta particle source and the second beta particle detector are arranged to measure a gas.

27. The device of claim 25, wherein:
 the first beta particle source is located approximate a first diameter of the flow line and a first source window, and the first beta particle detector is located approximate the first diameter of the flow line and a first detector window; and
 the second beta particle source is located approximate a second diameter of the flow line and a second source window, and the second beta particle is located approximate the second diameter of the flow line and a second detector window.

28. The device of claim 27, wherein a processor is in communication with the first beta particle detector and the second beta particle detector, the processor receives a first pulsed signal from the first beta particle detector and a second pulsed signal from the second beta particle detector, and the processor processes the received first and second pulsed signals to determine the at least one property of the fluid.

29. The device of claim 27, wherein the device is configured to be deployed downhole and the beta particle source mounted within the pressure housing generates particles that pass into the fluid within one of a downhole environment, a reservoir, or in a borehole.

30. The device of claim 1, wherein the beta particle detector is a solid state beta particle detector.

31. The device of claim 30, wherein the solid state beta particle detector comprises a wide band gap material.

32. The device of claim 31, wherein the solid state beta particle detector comprises a diamond material.

33. The device of claim 1, wherein the flow line is configured to withstand pressures within the flow line of at least 10 kpsi.

34. The device of claim 1, wherein the flow line is configured to withstand pressures within the flow line of at least 15 kpsi.

35. The device of claim 1, wherein the beta particle source produces beta particles with an energy less than 3 MeV.

36. The device of claim 1, wherein the at least one source window and the at least one detector window are pressure compensated by the at least one pressure compensated chamber.

37. A device for measuring at least one property of a fluid, wherein the at least one property includes density, the device comprising:
 a pressure housing comprising:
  a flow line for containing the fluid;
  at least one solid state beta particle detector;
  at least one beta particle source configured to generate beta particles that pass through the fluid and are detected by the solid state beta particle detector; and
  at least one pressure compensated chamber, wherein the at least one solid state beta particle detector and the at least one beta particle source are located within the at least one pressure compensated chamber.

38. The device of claim 37, further comprising:
 a processor in communication with the solid state beta particle detector, wherein the processor receives a pulsed signal from the solid state beta particle detector, the processor processes the received pulsed signals, and the processor determines the at least one property of the fluid.

39. The device of claim 37, wherein the solid state beta particle detector comprises a wide band gap material.

40. The device of claim 39, wherein the solid state beta particle detector comprises a diamond material.

41. The device of claim 37, further comprising:
 at least one source window;
 at least one detector window; and
 wherein the at least one source window and the at least one detector window are pressure compensated by the at least one pressure compensated chamber.

42. A method for measuring at least one property of a fluid, wherein the at least one property includes density, the method comprising:
 generating beta particles using a beta particle source, wherein the beta particles pass into the fluid;
 detecting the beta particles that have passed into the fluid using a solid state beta particle detector, wherein the at least one solid state beta particle detector and the at least one beta particle source are located within at least one pressure compensated chamber;
 receiving a pulsed signal from the solid state beta particle detector; and
 determining the at least one property of the fluid using the pulsed signal.

43. The device of claim 37, wherein the flow line is configured to withstand pressures within the flow line of at least 5 kpsi.

* * * * *